United States Patent [19]

Berger

[11] Patent Number: 5,658,310

[45] Date of Patent: *Aug. 19, 1997

[54] BALLOON COMPRESSOR FOR INTERNAL FIXATION OF BONE FRACTURES

[76] Inventor: J. Lee Berger, 895 Mohawk Rd., Franklin Lakes, N.J. 07417

[ * ] Notice: The term of this patent shall not extend beyond the expiration date of Pat. No. 5,423,850.

[21] Appl. No.: 464,294

[22] Filed: Jun. 5, 1995

Related U.S. Application Data

[63] Continuation-in-part of Ser. No. 153,030, Nov. 17, 1993, Pat. No. 5,423,850, which is a continuation-in-part of Ser. No. 130,434, Oct. 1, 1993, Pat. No. 5,480,400.

[51] Int. Cl.$^6$ ............................................. A61M 29/00
[52] U.S. Cl. ..................... 606/192; 606/60; 604/96
[58] Field of Search .................... 606/60, 62, 191, 606/192, 194, 155, 92–95; 604/96; 128/DIG. 20

[56] References Cited

U.S. PATENT DOCUMENTS

| | | | |
|---|---|---|---|
| 3,223,083 | 12/1965 | Cobey | 606/60 |
| 3,564,078 | 2/1971 | Wicker, Jr. et al. | 606/60 |
| 3,760,802 | 9/1973 | Fischer et al. | |
| 3,779,239 | 12/1973 | Fischer et al. | |
| 4,227,518 | 10/1980 | Aginsky | |
| 4,275,717 | 6/1981 | Bolesky | |
| 4,313,434 | 2/1982 | Segal | 606/62 |
| 4,457,301 | 7/1984 | Walker | |
| 4,467,794 | 8/1984 | Maffei et al. | |
| 4,946,459 | 8/1990 | Bradshaw et al. | |
| 4,969,888 | 11/1990 | Scholten et al. | 606/60 |
| 5,002,543 | 3/1991 | Bradshaw et al. | |
| 5,034,013 | 7/1991 | Kyle et al. | |
| 5,102,413 | 4/1992 | Poddar | |
| 5,104,399 | 4/1992 | Lazaros | |
| 5,108,404 | 4/1992 | Scholten et al. | |
| 5,263,931 | 11/1993 | Miller | |
| 5,303,718 | 4/1994 | Krajicek | 606/60 |
| 5,423,850 | 6/1995 | Berger | 606/192 |

FOREIGN PATENT DOCUMENTS

| | | |
|---|---|---|
| 9110407 | 7/1991 | European Pat. Off. |
| 824377 | 7/1949 | Germany |
| 3347333 | 6/1984 | Germany |
| 3924610 | 3/1990 | Germany |

Primary Examiner—Michael Buiz
Assistant Examiner—William W. Lewis
Attorney, Agent, or Firm—John S. Hale; Gipple & Hale

[57] ABSTRACT

The present invention is directed toward a method and apparatus for performing an internal fixation of fractures of tubular bones using a balloon catheter fixation device which is guided and transported through the medullary canal and fracture site of the bone by a plurality of guide wires mounted in said balloon catheter fixation device. A bone cement is applied to the fracture site and the balloon catheter is inflated inside the bone and tightened by applying pressure on the catheter outside of the bone by tightening the catheter tube and holding the same in place in an inflated condition to apply a compression force across the fracture site enhancing the stability of the fractured bone and promoting osseous healing.

23 Claims, 2 Drawing Sheets

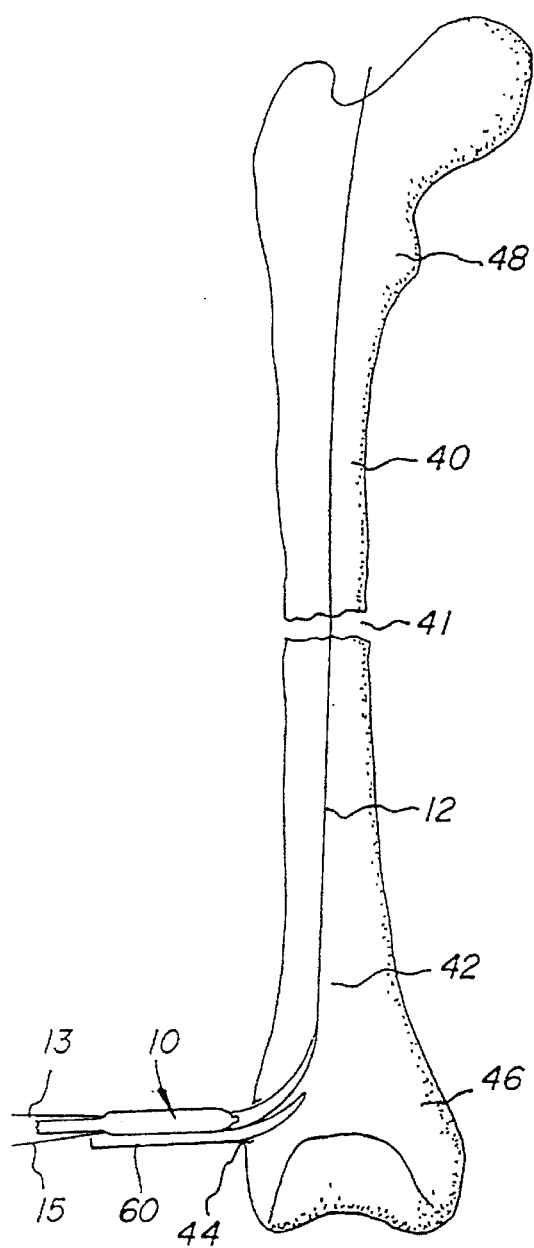
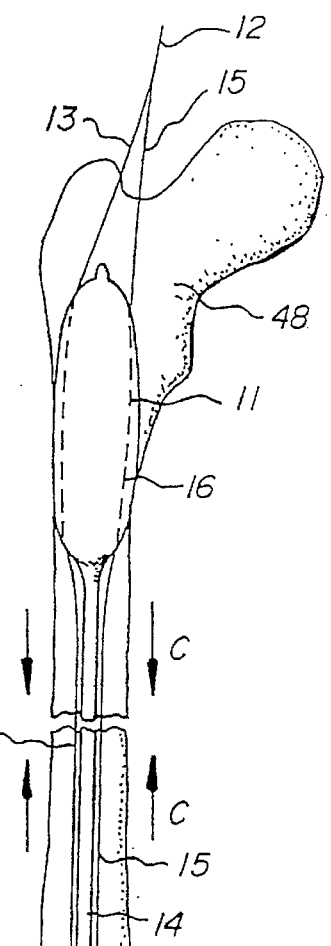
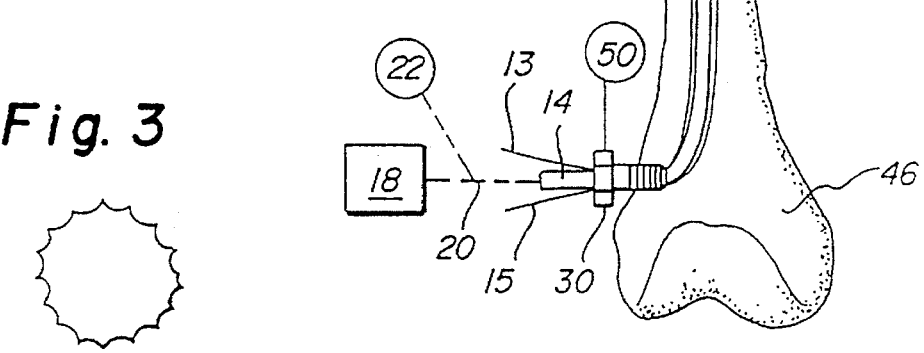
Fig. 1
Fig. 2
Fig. 3

BALLOON COMPRESSOR FOR INTERNAL FIXATION OF BONE FRACTURES

RELATED CASES

This is a continuation-in-part of U.S. patent application No. 08/153,030, filed Nov. 17, 1993, U.S. Pat. No. 5,423, 850, issued Jun. 13, 1995, which is continuation-in-part of U.S. patent application No. 08/130,434, filed Oct. 1, 1993, now U.S. Pat. No. 5,480,400.

BACKGROUND OF THE INVENTION

1. Field of the Invention

The present invention is generally directed toward an apparatus for the internal fixation of fractures of tubular bones by compression.

2. Brief Description of the Background

Currently, fractured tubular bones are transfixed surgically by either metal plates and screws or intramedullary metal rods.

It is known that with internal fixation of fractures with plate and screw devices it is desirable to apply a compressive force across the fracture site. Bone is a viscoelastic material and support of the structure and transmission of load is the mechanical function of bone. Bone is strongest in compression and weakest in tension. When a compressive force is applied across a fracture site it allows the fractured segments of bone to be placed in close proximity and the compressive force stimulates the bone in healing. If compression is applied at the fracture site, the intimate contact of the bone fragments restores the structural stability of the bone and allows the direct transfer of force from fragment to fragment rather than only through the implant. A compressive force applied directly at the fracture site hastens the healing of bone by encouraging the formation of new osteons which bridge the fracture line promoting a primary type of bone healing.

Some bone fracture realignment procedures involve insertion of a wire into the medullary canal which is then guided through the bone segments often in conjunction with a partially inserted nail for leverage. When the segments are aligned, the nail is fully inserted and the wire is withdrawn.

Metal intramedullary devices, which function as internal splints, have been used for many years to align fractures of tubular bones. These devices may take the form nails, U.S. Pat. No. 5,034,013; tubular members, U.S. Pat. No. 4,467, 794; or a multiple pin device, U.S. Pat. No. 4,457,301. A steerable intramedullary fracture reduction device having an elongated shaft with a steerable tip pivotally mounted to the distal end of the shaft is shown by U.S. Pat. No. 5,002,543. In this patent, a tip actuating apparatus near the proximal end of the shaft enables the operator to steer the tip and the shaft into successive segments of the fractured bone, even when the segments are transversely or rotationally displaced so that the segment can be aligned by the shaft. Metal compression devices which are used for fractures are shown by U.S. Pat. Nos. 4,275,717; 4,227,518; 3,779,239 and 3,760, 802. The aforenoted metal compression devices are generally directed towards a threaded rod which is inserted within the medullary canal of a fractured tubular bone. The rod is provided with a distal end having an expandable spreadable sheath or fingers which expand upon rotation of the rod. The proximal end of the rod is located outside of the bone and is provided with a nut which holds the rod in place inside the bone thereby causing the fractured bone portions to be held together. U.S. Pat. No. 4,946,459 shows an intramedullary device for fixing and extending separated portions of a long bone within the body of a patient. The device has a tubular sleeve which is nailed to one end of the bone and an adjustment assembly with a moveable member which bears against an end of the nail. The moveable member can be moved from outside the patient to adjust the separation between the portions of the fractured bone.

The aforementioned prior art devices have metal fingers or sleeves which engage the walls of the medullary canal of the bone with deleterious effects.

The use of such prior art intramedullary devices involves the reaming of the medullary cavity which has the effect of destroying the inner lining of blood vessels. Furthermore the ends of long bones in children are also the growth center of the bones. Drilling or gouging through the ends causes damage and may stop or deform further growth.

Other prior art devices currently use dynamic compression plates and screw devices to apply compression across the fracture site. However, for insertion of this type of device, it is necessary to make a large surgical incision over the outer cortex of the bone directly at the fracture site. Placing this type of fixation device entails the disturbance of the soft tissues overlying the fracture site, disturbance of the fracture hematoma, and stripping the periosteium of bone which compromises the blood supply to the bone at the fracture site.

A flexible bladder device has been described by U.S. Pat. No. 4,313,434 to align fractures intramedullarly. However, this bladder device is designed to be placed directly at the fracture site to provide fixation. The bladder device was not designed for compression at the fracture site and when inflated at the fracture site actually promotes separation of the fracture fragments and has the opposite effect of the present balloon catheter compression device.

There is no known intramedullary device currently available that applies a compressive force at the fracture site in addition to aligning the fracture.

SUMMARY OF THE INVENTION

An improved method and apparatus for treatment of fractures of tubular bones relies on the principle of compressive force to align fractures of tubular bones and to promote and hasten the healing of such fractures. The intramedullary balloon of the balloon catheter is designed to be guided and transported through the medullary canal of the bone and placed either proximal or distal to the fracture site. The balloon when inflated with sterile saline solution is held securely in place in the medullary canal of the bone acting as an intramedullary anchor for the balloon catheter. It is the elastic property of the catheter that when tightened against the rigid immobile force of the anchoring balloon allows the fractured segments of the bone to align and come in intimate contact. With further tightening of the catheter a compressive force is applied across the fracture site.

It is an object of the invention to provide a fracture compression device which minimizes damage to the interior blood vessels and periosteium of the bone and allows the guide wire to be removed.

It is another object of the invention to provide a fracture compression device which utilizes a bioabsorbable bone cement in combination with the compressive force to set the fracture site.

It is another object of the invention to provide a fracture compression device which utilizes a quick hardening biomaterial such as Norjan SRS in combination with the compressive force to set the fracture site.

In the accompanying drawings, there is shown an illustrative embodiment of the invention from which these and other objectives, novel features and advantages will be readily apparent.

BRIEF DESCRIPTION OF THE DRAWINGS

FIG. 1 is a cross sectional schematic of the invention showing insertion of the inventive balloon catheter device into the bone;

FIG. 2 is a cross sectional schematic of the invention showing fixation of the balloon catheter in the medullary canal of the bone and compressive tightening of the fractured portions of the bone with the sensing and fluid transmission elements shown in block diagram;

FIG. 3 is a cross section of the inflated balloon with a fluted outer wall; and

DETAILED DESCRIPTION OF THE INVENTION

Figure 4:
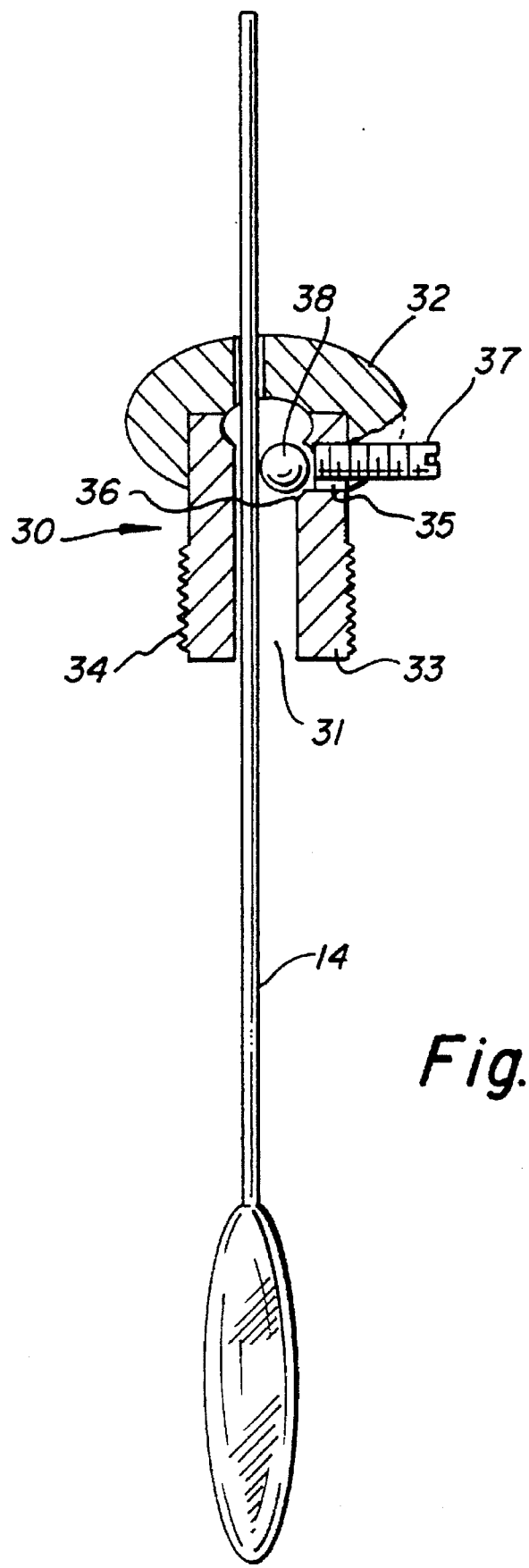
FIG. 4 is a cross section schematic of the fixation post with balloon catheter extending therethrough.

A preferred embodiment and best mode of the invention is shown in FIGS. 1 and 2. The intramedullary balloon compression device 10 is used to treat fractures of tubular bones by applying intramedullary compression at the fracture site.

When a tubular bone 40 is fractured at a fracture site 41, the catheter device 10 can be inserted into the medullary canal 42 of the bone through a small incision either proximal or distal to the site of the fracture via a catheter introducer. A small aperture 44 is made in the outer cortex of the bone portion 46 with an introducing bone drill and drill bit or bone awl to access the medullary canal of the bone. Once the aperture 44 is created in the bone, the balloon catheter device 10 with lead wire 12 and double guide wires 13 and 15 or additional guide wires if such are needed is inserted into the medullar cavity of the bone by a catheter introducer 60. The balloon compression device 10 is preferably constructed of a plastic extruded material such as polyethylene, teflon, kevlar or other durable material is then guided by the guide wires 13 and 15 past the fracture site 41 into the other portion 48 of the fractured bone. The balloon catheter device 10 is formed with a plurality of lumens 11 along its length for guide wire insertion. Location of the lumens 11 are shown in phantom in FIG. 2. The guide wires may be removable from the balloon catheter or permanently incorporated in the catheter. The balloon 16 of the catheter device is inflated to its maximum diameter via the elastic catheter tube 14 with sterile saline solution by means of a syringe 18, associated feed tube 20 and a balloon pressure gauge monitor 22 as shown by respective block diagrams. It is envisioned that the shape of the balloon 16 can be modified in various forms, including smooth, fluted as shown in FIG. 3 or ridged outer walls for promoting endosteal blood supply at the site of the balloon insertion. The inflated balloon 16 is held securely in place by the positive pressure applied to the intramedullary walls of the bone. Once the balloon 16 is anchored in place past the fracture site 41, the attached catheter tube 14 can be tightened.

If desired a bone-mineral substitute, bone cement or bioabsorbable bone cement can be applied to the fractured bone ends prior to application of the compression force. One suitable bone-mineral substitute is a calcium phosphate compound with a sodium phosphate solution. Monocalcium phosphate, monohydrate, triacalcium phosphate and calcium carbonate are dry mixed and a sodium phosphate solution is added to form a paste which is malleable and hardens in about 10 minutes. After implantation the paste hardens and turns into carbonated apatite.

The catheter tensioning device is provided with a calibrated force measuring device such as a strain gauge 50 to measure the compression force. The tightening of the catheter 14 with the fixed balloon 16 in place aligns the fracture and compresses the proximal and distal portions 46 and 48 of the fractured bone together. After alignment and compression of the fracture with the intramedullary balloon compression catheter, the catheter 14 is secured firmly to the bone 46 at it's insertion site 44 with a screw, post or peg type of fixation device 30. Thus, the balloon compression catheter can be incorporated into existing bone fixation technology such as an intramedullary rod, a fixation screw or plate, hip screw or total joint arthroplasty that uses a balloon catheter to enhance fixation to the bone. Preferably, the post 30 is hollow with a head 32 and stem 33 which is exteriorly threaded at 34. The stem 33 defines a throughgoing bore 35 with leads into lumen 31 and opens into an arcuate ball seat 36 which is cut into the lumen wall. The bore 35 is threaded to receive a fixation screw 37 which is used to tighten a crimping ball 38 to crimp the catheter tube 14 within the fixation port. The crimping ball 38 can be instructed of metal or plastic. The catheter tube 14 extending through the lumen 31 of the post is thus clamped or affixed to the bone fixation post. The fixation post 30 and catheter 14 can be respectively released and tightened, if necessary, to apply further compression at the fracture site.

In operation, the fixation post, which may be smooth and possibly threaded, fits into the aperture that was cut in the bone for insertion of the balloon catheter. The catheter is inserted through the hollow center of the head 33 and lumen 31 of the shaft portion of the fixation post. After the catheter is guided past the fracture site in the medullary canal of the bone by guide wires, the balloon portion of the catheter is inflated away from the fracture site and in doing so does not compromise the extramedullary periosteal blood supply or the intramedullary blood supply at the fracture site. The compression force of the catheter allows the fractured fragments of bone to be aligned in close apposition promoting healing of the fracture similar to the prior art dynamic compression plate device without making an incision at the fracture site and without compromising the blood supply at the fracture site. The device does not disturb the fracture hematoma which is essential for healing of the fracture. A tensioning device fits over the head 33 of the fixation post. At this stage bone cement or bone-mineral substitute can be applied. The balloon catheter is then tightened with the tensioning device. This reduces the fracture distance, applying compression at the fracture site. After the bone is aligned and compressed at the fracture site, the crimping ball 38, which lies in a separate tunnel or bore 35 within the shaft of the fixation post is tightened with the threaded set screw 37. When tightened against the tube of the catheter, the crimping ball 38 occludes the central lumen of the catheter tube 14 keeping the balloon 16 inflated thus securing the catheter within the shaft of the fixation post.

After the fracture is healed, or alternatively in some cases after the bone cement has set up, the set screw can be released, the balloon deflated and the catheter and fixation post can be easily removed from the bone. If necessary, additional balloon catheters can be similarly positioned in place for fixation. The balloon compression catheter can be used independently for the intramedullary compression fixation of tubular bones or can be used as a supplement with bioabsorbable bone cement or to metal intramedullary devices to apply compression across the fracture site.

The intramedullary balloon compression catheter is designed specifically to apply a compressive force at the fracture site, to align the fractured bone and promote healing of the fracture.

Osteogenesis is promoted by compression across a fracture site and the intramedullary balloon compression catheter facilitates this in an intramedullary fashion.

In the foregoing description, the invention has been described with reference to a particular preferred embodiment, although it is to be understood that specific details shown are merely illustrative, and the invention may be carried out in other ways without departing from the true spirit and scope of the following claims:

What is claimed:

1. An assembly for setting fractured bones comprising a balloon catheter with a tubing having an inner lumen and an inflatable balloon secured to said tubing at the distal end thereof, said balloon being in fluid communication with the lumen of said tubing, a guide wire mounted to said balloon and means separate from said balloon catheter adapted to be mounted in a portion of said fractured bone distal from said balloon to receive said tubing and hold said balloon catheter when said balloon is inflated in a fixed stressed condition to provide compression on the fracture side of fractured bone portions and a fluid discharge means connected to said balloon catheter and communicating with said tubing lumen to allow fluid discharge from said fluid discharge means into said tubing lumen to inflate the balloon of said balloon catheter.

2. The assembly of claim 1 including a pressure monitoring means connected to said balloon catheter and communicating with said tubing lumen to measure the pressure of the inflated balloon of said catheter.

3. The assembly of claim 1 wherein said catheter tubing is flexible and reinforced.

4. The assembly of claim 1 wherein said catheter tubing is elastic and constructed of teflon.

5. The assembly of claim 1 wherein said balloon has fluted sides.

6. The assembly of claim 1 wherein said fluid is a saline solution.

7. An assembly for setting fractured bones comprising a balloon catheter with a tubing having an inner lumen and an inflatable balloon secured to said tubing at the distal end thereof, said balloon being in fluid communication with the lumen said tubing, a guide wire mounted to said balloon and means separate from said balloon catheter adapted to be mounted in a portion of said fractured bone distal from said balloon to receive said tubing and hold said balloon catheter when said balloon is inflated in a fixed stressed condition to provide compression on the fracture side of fractured bone portions and a fluid discharge means connected to said balloon catheter and communicating with said tubing lumen to allow fluid discharge from said fluid discharge means into said tubing lumen to inflate the balloon of said balloon catheter, said means adapted to be mounted in a portion of said fractured bone is a hollow post member with external screw threads.

8. The assembly of claim 7 wherein said hollow post member adapted to be mounted in a portion of said fractured bone includes set screw means moveably mounted therein.

9. The assembly of claim 8 wherein said set screw means comprises a ball seat defined by said hollow post, a throughgoing channel formed in said hollow post member leading into said ball seat, a ball seated in said ball seat and a set screw moveably mounted in said throughgoing channel adapted to engage and move said ball.

10. An assembly for setting a fractured bone by holding the fractured bone portions together under a compression force across the fracture site comprising a balloon catheter with a tubing having an inner lumen and an inflatable balloon secured to said tubing and being in fluid communication with the lumen of said tubing, said balloon catheter being sized to move within the medullary cavity of the bone, a guide wire mounted to said balloon and mounting means adapted to be mounted in a portion of said fractured bone distal from said balloon, said mounting means selectively engaging said tubing and holding said tubing in a fixed stressed condition to provide compression on the fracture site of fractured bone portions after said balloon has been inflated inside one of said bone portions, and means connected to said tubing allowing the inflation of said balloon with fluid.

11. An assembly for setting a fractured bone by holding the fractured bone portions together under a compression force across the fracture site comprising a balloon catheter with a tubing having an inner lumen and an inflatable balloon secured to said tubing and being in fluid communication with the lumen of said tubing, said balloon catheter being sized to move within the medullary cavity of the bone, a guide wire mounted to said balloon and mounting means adapted to be mounted in a portion of said fractured bone distal from said balloon, said mounting means selectively engaging said tubing and holding said tubing in a fixed stressed condition to provide compression on the fracture site of fractured bone portions after said balloon has been inflated inside one of said bone portions, said mounting means comprises a post member with a throughgoing lumen and set screw means threadably mounted to said post member and extending into said lumen and means connected to said tubing allowing the inflation of said balloon with fluid.

12. The assembly of claim 11 wherein said set screw means comprises a ball seat defined by said post member communicating with said lumen, a throughgoing channel cut in said post member leading into said ball seat, a ball seated in said ball seat and extending into said lumen and a set screw moveably mounted in said throughgoing channel adapted to engage and move said ball into said lumen.

13. An assembly for setting a fractured bone by holding the fractured bone portions together under a compression force across the fracture site comprising an expandable catheter device with a tubing sized to move within the medullary cavity of the bone, a guide wire mounted to said expandable catheter device and mounting means adapted to be mounted in a portion of said fractured bone distal from said expandable catheter device, said mounting means selectively engaging said tubing and holding said tubing in a fixed stressed condition to provide compression on the fracture site of fractured bone portions after said expandable catheter device has been expanded inside one of said bone portions, and means connected to said tubing means allowing the expansion of said expandable catheter device.

14. The assembly of claim 13 wherein said mounting means comprises a post member with a throughgoing lumen and set screw means threadably mounted to said post member and extending into said lumen.

15. The assembly of claim 13 wherein said tubing is elastic.

16. A method of setting a fractured bone by compression comprising the steps of:

a) cutting an aperture into one portion of the fractured bone away from the site of the fracture allowing communication with the medullary canal of the bone;

b) securing a hollow fixation post means in said aperture;

c) inserting a balloon catheter device and catheter guide wire means through the fixation cut in the bone into the medullar cavity of the bone;

d) transporting the balloon catheter in the medullary canal of the bone past the fracture site by use of the catheter guide wire means to a point distal from the fractured site;

e) inflating the balloon of the balloon catheter device to its maximum diameter so that the balloon catheter device is held securely in place by the positive pressure of the balloon applied to the intramedullary walls of the bone;

f) applying bone cement material to at least one fracture site of the bone; and g) tightening the attached catheter with the fixed balloon in place to align the fracture and compress the proximal and distal portions of the fractured bone together.

17. The method of claim 16 wherein said application step of applying bone cement material comprises injecting said bone cement material into said fracture site and allowing the bone cement material to harden.

18. The method of claim 16 wherein said tightening step uses a threaded fixation screw means as the securing device.

19. A method of setting a fractured bone by compression comprising the steps of:

a) cutting an aperture into one portion of the fractured bone away from the site of the fracture allowing communication with the medullary canal of the bone;

b) securing a hollow fixation post means in said aperture;

c) inserting a balloon catheter device and catheter guide wire means through the fixation cut in the bone into the medullar cavity of the bone;

d) transporting the balloon catheter in the medullary canal of the bone past the fracture site by use of the catheter guide wire means to a point distal from the fractured site;

e) inflating the balloon of the balloon catheter device to its maximum diameter so that the balloon catheter device is held securely in place by the positive pressure of the balloon applied to the intramedullary walls of the bone;

f) applying bone cement material to at least one fracture site of the bone; and g) tightening the attached catheter with the fixed balloon in place to align the fracture and compress the proximal and distal portions of the fractured bone together, said tightening step using a threaded fixation screw means as the securing device, and said fixation screw means includes a ball and ball camming means to engage and secure the balloon catheter.

20. The method of claim 19 wherein said bone cement material is a bone-mineral substitute.

21. The method of claim 19 wherein said bone cement material is biodegradable.

22. A method of setting a fractured bone by compression comprising the steps of:

a) cutting an aperture into one portion of the fractured bone away from the site of the fracture allowing communication with the medullary canal of the bone;

b) securing a hollow fixation post means in said aperture;

c) inserting an expandable catheter device and catheter guide wire means through the fixation post means cut in the bone into the medullar cavity of the bone;

d) transporting the expandable catheter device in the medullary canal of the bone past the fracture site by use of the catheter guide wire means to a point distal from the fractured site;

e) expanding the expandable catheter device against the intramedullary walls of the bone so that pressure is uniformly exerted on the bone so that the catheter device is held securely in place by the positive pressure of the expanded device applied to the intramedullary walls of the bone;

f) applying bone cement material to at least one fracture site of the bone;

g) tightening the catheter device with the expanded catheter device secured in place to align the fracture and compress the proximal and distal portions of the fractured bone together; and h) securing the catheter device in the tightened position.

23. The method of claim 22 wherein said application step of applying bone cement material comprises injecting said bone cement material into said fracture site and allowing the bone cement material to harden.

* * * * *